United States Patent [19]

Sweeny et al.

[11] 3,943,146
[45] Mar. 9, 1976

[54] SULFUR DIOXIDE - IMIDAZOLE ADDUCTS

[75] Inventors: Norman P. Sweeny, North Oaks, Minn.; Karl Friedrich Thom, Cologne, Germany

[73] Assignee: Minnesota Mining and Manufacturing Company, St. Paul, Minn.

[22] Filed: Feb. 26, 1974

[21] Appl. No.: 445,862

Related U.S. Application Data

[62] Division of Ser. No. 262,557, June 14, 1972, Pat. No. 3,839,282.

[52] U.S. Cl............................... 260/309.2; 260/309
[51] Int. Cl.²....................................... C07D 235/04
[58] Field of Search......................... 260/309, 309.2

[56] References Cited
UNITED STATES PATENTS 3,502,578  3/1970  Raifsnider....................... 260/309.6

OTHER PUBLICATIONS

Die Makromolekulare Chemie, 126 : 16–22, (1969), Matsuda et al.

*Primary Examiner*—Sherman D. Winters
*Attorney, Agent, or Firm*—Alexander, Sell, Steldt & DeLaHunt

[57] ABSTRACT

The disclosed compounds are adducts of imidazole or derivatives thereof and sulfur dioxide. The adducts are apparently of the Lewis acid-Lewis base type, and are useful as latent curing agents for epoxide resins. The adducts are prepared by interacting the imidazole and sulfur dioxide under anhydrous conditions. Equimolar imidazole-$SO_2$ adducts can serve as a source of sulfur dioxide at room temperature.

3 Claims, No Drawings

SULFUR DIOXIDE - IMIDAZOLE ADDUCTS

This is a division of application Ser. No. 262,557, filed June 14, 1972, now U.S. Pat. No. 3,839,282.

FIELD OF THE INVENTION

This invention relates to sulfur dioxide-imidazole adducts and methods for making them, the "imidazole" portion of the adduct being either imidazole itself ($C_3H_4N_2$) or a derivative thereof. An aspect of this invention relates to latent epoxy curing agents and latent curable epoxide resin systems containing sulfur dioxide-imidazole adducts. A further aspect of this invention relates to a source for an acid stabilizer in a closed system.

DESCRIPTION OF THE PRIOR ART

It is well known that sulfur dioxide is a Lewis acid, though not nearly so strong a Lewis acid as, for example, boron trifluoride. It is also known that nitrogen bases (e.g. amines) are Lewis bases and can react with sulfur dioxide to form adducts. The literature relating to such adducts is extensive, representative examples being W. C. Fernelius, Ed., *Inorganic Synthesis* II, McGraw-Hill, N.Y. (1946); W. E. Byrd, Inorganic Chemistry 1, p. 762 (1962); K. R. Hoffman et al, J. Am. Chem. Soc. 68, p. 997 (1946), H. A. Hoffman et al, J. Am. Chem. Soc. 70, p. 262 (1948). The Byrd article indicates that the exact structure of aromatic amine-sulfur dioxide complexes is not well understood, since it is possible that the sulfur dioxide could be bound to the adduct via the pi-complex of the aromatic ring. The picture is further complicated by data in the Byrd article and both Hoffman et al articles indicating that some of these aromatic (or heterocyclic-aromatic) amine-sulfur dioxide adducts or complexes are unstable, though there is little doubt that true adducts, rather than simple mixtures, are formed.

According to U.S. Pat. No. 3,270,490 (Wood), issued January 1942, morpholine and sulfur dioxide react to form a compound useful as a photographic developer, local anesthetic, or antioxidant, but in this case it is suggested that the compound can be a true salt, i.e. a salt of the cation-anion type. Some of the aromatic amine-sulfur dioxide adducts exhibit crystalline character and have sharp melting points, but probably lack this high degree of ionic character. The nature of the amine (aliphatic, aromatic, aromatic heterocyclic, nonaromatic heterocyclic, etc.) appears to have significant effects upon the nature of the sulfur dioxide adduct or compound, but these effects have not been explored fully enough to postualte any general rules for all the possible adducts.

Apparently none of these prior art adducts or compounds has been investigated for use as a latent catalyst or initiator or curative in epoxy resin technology, though amines per se have been investigated extensively. Several different Lewis acid-Lewis base adducts of the amine-boron trifluoride type have been carefully studied by epoxy resin chemists, and various theories have been proposed to explain their potency or latency, as the case may be, in curing diglycidyl ether-bisphenol A epoxides at various cure temperatures. See, for example, Harris et al, J. Appl. Polymer Science 10, p. 523 (1966). The Harris et al article provides little or no guidance for one attempting to use a Lewis acid-Lewis base adduct derived from sulfur dioxide instead of boron trifluoride. The degree of latency of an amine-$BF_3$ adduct appears to be independent of its stability (Harris et al, op cit., pp. 523–525 and 527), but the stability of amine-$SO_2$ adducts is so variable that latency might very well be a function of the stability of the adduct.

Imidazole and its derivatives have been used as non-latent initiators or curative-catalysts for epoxide resins, and various approaches have been used to make latent compounds or complexes containing imidazole nuclei; see, for example, U.S. Pat. No. 3,553,166 (Anderson et al), issued Jan. 5, 1971. Apparently, imidazole-sulfur dioxide adducts have never been reported in the literature and have never been proposed for use as epoxy curing agents or for any other purpose. In view of the variations in the stability of different types of aminesulfur dioxide adducts and the lack of guidance in the prior art as to their behavior as epoxy initiators, it would be difficult at best to predict the stability and utility of an imidazole-sulfur dioxide adduct. Nor is it even possible to predict with certainty from the available prior art if such an adduct can even be made and what its structure might be. Analogies between imidazole and other heterocyclic and/or aromatic and/or aliphatic amines are difficult to draw, due to the uniqueness of the imidazole nucleus

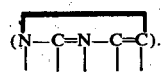

Accordingly, this invention contemplates synthesizing adducts from imidazole or derivatives thereof and sulfur dioxide. This invention further contemplates using these adducts in polymer chemistry and formulating either curable latent epoxy resin systems or stabilized acrylate monomers containing the adducts.

SUMMARY OF THE INVENTION

Briefly summarized, the present invention involves the synthesis of imidazole-sulfur dioxide adducts and the discovery that these adducts are useful both as a source for an acidic stabilizer and in the formulation of latent curable epoxides. These latent curable systems have a shelf life of weeks or months (e.g. at least 6 months) and are rendered non-latent at elevated temperatures (e.g. above 50° C., preferably above 130° C.); that is, the typical epoxide curing reactions can be made to occur expeditiously at these elevated temperatures. The compounds of this invention can be prepared by exposing imidazole or a derivative thereof (optionally dissolved in a solvent) to liquid or gaseous sulfur dioxide, or a saturated solution thereof, under anhydrous conditions for a period of several minutes until the compound precipitates out as a solid sulfur dioxide-imidazole adduct. The apparent behavior of these solid products in the presence of curable epoxy resins is evidence not only of utility, but also of a stable, adduct-like structure, as opposed to a mere physical mixture. The adducts decompose upon heating into sulfur dioxide and imidazole (or an imidazole derivative) and thereby serve as a latent source for either the imidazole or sulfur dioxide.

DETAILED DESCRIPTION

Adduct-like compounds made according to the present invention can be represented by the following formula:

(Imid)$_n$·SO$_2$           (I)

wherein Imid is imidazole or a derivative thereof, i.e. a nucleus of the formula

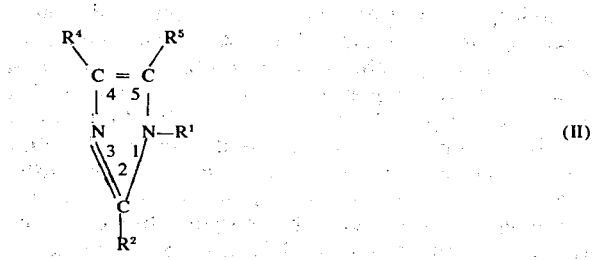

(II)

The $n$ term represents a small number less than 4, preferably an integer. The exact structure of the various species encompassed by $n$ is not a known, but available evidence substantiates the formation of Lewis acid-Lewis base adducts wherein $n=1$, 2, or 3 or mixtures of these species. When $n=1$, these compounds have a tendency to lose sulfur dioxide slowly until the $n=2$ species (the most stable) is formed.

The terms $R^1$, $R^2$, $R^4$, and $R^5$ represent suitable substituents or hydrogen, the preferred substituents being nonhindering organic radicals such as alkyl or aryl radicals or, particularly in the case of $R^4$ and $R^5$, fused rings. For convenience, the term "an imidazole" or "an imidazole nucleus" is used in this specification to denote both imidazole itself ($C_3N_2H_4$) and the imidazole derivatives of formula (II), set forth previously.

The term "curing agent" is used to denote agents which assist or participate in hardening or crosslinking or polymerization reactions which solidify or increase the viscosity of liquid epoxide monomers or prepolymers or convert solid epoxides to tough, durable thermoset materials. "Curing agents" are referred to as "hardeners" or "crosslinkers" in some contexts, because of their ability to convert even the liquid monomers or prepolymers to thermoset solids. It is also common in the art to refer to imidazole as a "catalyst" or "initiator" since it assists in the opening of the oxirane ring. However, it is established that imidazole can make a contribution to the properties of the cured epoxide and is thus more than a simple catalyst. For consistency of terminology, the term "curing agent" is used in this specification.

In the art of curing or hardening epoxide resins, a "latent" curing agent is one which is effective only under certain specific conditions, e.g. temperatures above 50° or 100° C. A latent curing agent can therefore be included in a one-part curable system which is storable for long periods of time at normal ambient temperatures, and the storable system can be said to have good storage stability or a long "shelf life" or "pot life". The shelf life of a liquid one-part system can be conveniently determined by observing its viscosity; any tendency toward premature gelation will, of course, be evidenced by an increase in viscosity.

Adducts of an imidazole and sulfur dioxide can be synthesized by one of the following methods, provided that anhydrous conditions are maintained.

1. An imidazole is dissolved in a solvent such as acetonitrile and gaseous sulfur dioxide is bubbled through the solution. An exothermic reaction occurs. Upon dilution with the solvent, a white precipitate forms which is the imidazolesulfur dioxide adduct.

2. Gaseous sulfur dioxide can be passed over an imidazole and the adduct forms. The solid adduct may be recovered from the reaction mass by treating it with a solvent.

3. A solution of an imidazole in a solvent can be added to another portion of a similar or the same solvent which is saturated with sulfur dioxide. A precipitate is formed which is the imidazole-sulfur dioxide adduct.

4. Liquid sulfur dioxide can be added to an imidazole (either as the pure compound or as a solution of the compound) and the adduct forms. The mixture is treated with a solvent to recover the solid adduct.

5. A solution of an imidazole can be placed in an autoclave and the autoclave pressurized with sulfur dioxide. The adduct precipitates out of solution.

The sulfur dioxide gas reactions may utilize diluent gases to act as carriers and controls for the exothermic reaction.

The 2:1 adducts (2 imidazole:1 SO$_2$) are more stable than the 1:1 adducts. Sulfur dioxide loss occurs with 1:1 adducts at room temperature over a period of three to four days. The equation for this decomposition is:

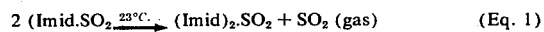
          (Eq. 1)

wherein Imid is as defined previously.

It is difficult to remove the last traces of solvent from the compounds of Formula (I), and mixture of compounds wherein n has more than one value, e.g. 2 and 3, can form.

The adduct-like compounds of this invention decompose or dissociate according to the following equation:

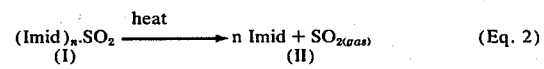
          (Eq. 2)

For a given "Imid" moiety, the dissociation temperatures of the compounds of formula (I) can vary when $n$ varies. For example, for 1,2-dimethylimidazole, the dissociation temperature of the $n=2$ species is higher than that of the $n=1$ species. The properties of cured epoxide systems which have been obtained by heating the curable latent systems containing formula (I) compounds can also vary with $n$ for a given "Imid" moiety. The dissociation temperatures are not fixed precisely, but generally appear to be significantly higher than room temperature. Under normal ambient temperature and pressure, e.g. 23° C./760 mm of Hg, dissociation of the 1:1 (i.e. $n=1$), 2:1 ($n=2$), and 3:1 ($n=3$) adducts according to Equation 2 is, to say the least, difficult to detect. Experimentation with curable epoxide materials such as diglycidyl ethers of bisphenol A shows that the adducts have little, if any, effect upon the viscosity of the epoxide over a period of months, indicating an epoxide pot life longer than 6 months. This pot life data indicates that little or no free imidazole or imidazole derivative is available for interaction with the vicinal epoxide (oxirane) ring, since free imidazole can cure typical curable epoxide systems in a manner of minutes at room temperature; see Farkas et al, J. Appl. Polym. Sci. 12, 159 (1968). Even the latentizing of imidazole with acetic acid to form imidazole acetate salts extends the pot life of the epoxide system to only about three weeks; see U.S. Pat. No. 3,356,645 (Warren), issued Dec. 5, 1967. Thus, a simple comparison with known curable epoxide systems provides further evidence that the adducts of the present invention are reasonably stable compounds at normal ambient temperature and pressure, at least insofar as loss of the imidazole moiety is concerned. Some clearly detectible loss of imidazole can occur at temperatures above the melting points of the adducts, particularly in the range of 100° – 200° C., as is subsequently shown by the data Table II. Since the adducts have varying degrees of stability at temperatures above 100° C., the rate or extent of dissociation can be selected in accordance with the desired rate of cure or gel time, as the case may be. To illustrate: given a temperature of 180° C. and a typical latent curable system containing a formula (I) compound of this invention, the gel time is much longer for "Imid" = benzimidazole than for "Imid" = imidazole ($C_3N_2H_4$). At 160° C., the benzimidazole adduct appears to have little or no effect upon a diglycidyl ether-bisphenol A epoxide prepolymer; but the imidazole adducts are very effective at this temperature. The 1-alkyl imidazole species of Formula (I) also exhibit longer gel times. The properties of the cured epoxides obtained according to this invention are generally satisfactory.

The compounds of Formula (I) are generally solids with fairly small melting ranges, typically not more than 5° Centigrade. These data can be compared to the 80°–85° C. melting range of morpholine-sulfur dioxide, which is reported to be a salt-like chemical compound in the U.S. Pat. No. 2,270,490 referred to previously. The compound $(Imid)_3 \cdot SO_2$, where Imid = 2-ethyl-4-methylimidazole, appears to be a viscous liquid, but, as shown subsequently by Table I, this is not typical.

Formulation of curable epoxide systems containing curing agents of this invention can be carried out along the lines generally laid down by latent imidazole epoxide curing technology, e.g. the technology described in the aforementioned U.S. Pat. Nos. 3,553,166 and 3,356,645. U.S. Pat. No. 3,553,166 also describes suitable co-curatives (e.g. of the dicyandiamide type) which can be included in the curable system. It is preferred to introduce at least 0.1% by weight, based on the weight of the epoxide monomer or prepolymer, of a compound of Formula (I) into the curable system, and levels of 1–20% by weight are particularly useful. Levels higher than 20% — even 50% or more — are permissible but excessively increase the cost of the system without any significant beneficial result.

Typical one-part curable epoxy resin systems formulated according to this invention comprise (1) 0.1 – 20 parts by weight of a curing agent of Formula (I), (2) at least 80 parts by weight of a suitable cycloaliphatic, aliphatic, aromatic, or heterocyclic epoxide, and (3) 0 – 300 parts by weight of suitable fillers, extenders, flexibilizers, pigments, and the like, e.g. colloidal silica. These one-part systems have sufficient shelf-life at normal ambient temperature to allow for most ordinary shipping and inventory procedures, although the stability of the system can be further enhanced, if desired, by special precautions such as careful temperature control during storage. It is generally not necessary to formulate two-part systems (with the epoxide in one container and the curing agent in another). If a two-part system is made up, however, the benefits of this invention will still be apparent to industrial users who blend the two parts and then carry out one or more coating, molding, laminating, casting, or impregnating steps prior to curing at cure temperatures above 100° C. These steps can be carried out in a leisurely fashion, taking advantage of the long room temperature "pot life" prior to curing at elevated temperatures.

Epoxides suitable for use in this invention can be aliphatic, cycloaliphatic, aromatic or heterocyclic and will typically have an average epoxy equivalency (i.e. the number of epoxy groups contained in the average molecule) of from about 1.7 to 6.0, preferably 2 or 3, this value being the average molecular weight of the epoxide divided by the epoxide equivalent weight. The epoxy equivalent weight, which is determined by multiplying the sample weight by 16 and dividing by the number of grams of oxirane oxygen in the sample, is typically greater than 100 for commercially useful curable systems. These materials are variously referred to as epoxide "monomers" or "prepolymers" and in any event can contain repeating units, e.g. repeating ether units. Typical of such epoxides are the glycidyl-type epoxy resins, e.g. the diglycidyl ethers of polyhydric phenols and of novolak resins, such as described in "Handbook of Epoxy Resins", by Lee and Neville, McGraw-Hill Book Co., New York (1967).

Another useful class of epoxides has a structure of the following type:

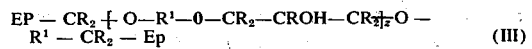  (III)

or

  (IV)

where
Ep is an epoxide ring,
R is hydrogen, or a non-hindering aliphatic group (e.g. methyl);
$R^1$ is a divalent aliphatic or aromatic radical; and
z is a number from 0 to about 5.
In Formula IV,
n is a number from 1 to 6.

Typically, these epoxides are glycidyl ethers of polyhydric phenols obtained by reacting a polyhydric phenol or aliphatic polyol with an excess of chlorohydrin, such as epichlorohydrin, e.g. the diglycidyl ether of Bisphenol-A or of resorcinol, 1,4-butane diol, or the like. Further examples of epoxides of this type which can be used in the practice of this invention are described in U.S. Pat. No. 3,018,262 (Schroeder), issued Jan. 23, 1962.

The preferred cycloaliphatic epoxide monomers or prepolymers preferably contain at least one 5- or 6-membered carbocylic ring (or heterocyclic ring with equivalent properties) on which is substituted the epoxide functional group. In polycyclic cycloaliphatic epoxides, the two rings are preferably independent and preferably joined by a bridging radical containing at least one ester or ether linkage. A plurality of these ester or ether linkages can provide flexibilizing properties in the cured system. Further examples of cycloaliphatic epoxide compounds are described in U.S. Pat. No. 3,117,099 (Proops et al), issued Jan. 7, 1964.

There are a host of commercially available epoxides which can be used in this invention, including the diglycidyl ether of Bisphenol-A (e.g. "Epon" 828, "EpiRez" 522-C, "Araldite" 7072, "Epon" 1002 and "DER" 332), mixtures of the diglycidyl ether of Bisphenol A with an alkyl glycidyl ether (e.g. "ERL" 2795), vinylcyclohexene dioxide (e.g. "ERL" - 4206), 3,4-epoxycyclohexylmethyl-3, 4-epoxycyclohexane carboxylate (e.g. "ERL"-4221), 3,4-epoxy-6-methylcyclohexylmethyl-3,4-epoxy-6-methylcyclohexane carboxylate (e.g. "ERL"-4201), bis(3,4-epoxy-6-methylcyclohexylmethyl)adipate (e.g. "ERL"-4289), bis(2,3-epoxycyclopentyl)ether (e.g. "ERL"-0400), aliphatic epoxy modified with polypropylene glycol (e.g. "ERL"-4050 and "ERL"-4052), dipentene dioxide (e.g. "ERL"-4269), epoxidized polybutadiene (e.g. "Oxiron" 2001), silicone epoxy (e.g. "Syl-Kem" 90), 1,4-butanediol diglycidyl ether (e.g. "araldite" RD-2), polyglycidyl ether of phenolformaldehyde novolak (e.g. "DEN"-431 and "DEN"-438) resorcinol diglycidyl ether (e.g. Ciba "ERE"-1359), and epoxidized unsaturated esters of carboxylic acids having more than six carbon atoms, e.g. expoxidized soybean oil. ("Epon" is a trade-mark of Shell Chemical Co.; "EpiRez" is a trademark of Jones-Dabney Co.; "Araldite" is a trademark of Ciba Products Co.; the various "DER" and "DEN" designations are trade designations of Dow Chemical Co.; the "ERL" designations are trade designations of Union Carbide Plastics Division; "Syl Kem" is a trade designation of Dow Corning; "Oxiron" is a trademark; and "ERE-1359" is a trade designation of Ciba Products Co.)

The compounds of Formula (I) and the nuclei of Formula (II) have already been described in some detail. As will be apparent from this description, the substituents $R^1$, $R^2$, $R^4$, and $R^5$ can be varied considerably without any adverse effect upon the operability of this invention. The teachings of the aforementioned U.S. Pat. Nos. 3,356,645 and 3,553,166, and of U.S. Pat. No. 3,631,150 (Green), issued Dec. 28, 1971, are generally applicable here with respect to selection of imidazole substituents, which can also include 5- and 6-member fused or separate heterocyclic or carbocyclic rings. Substitution at the 1- position (i.e. $R^1 \neq H$) is least preferred. Lower alkyl substituents (including substituted lower alkyl) are generally most preferred, although higher alkyl substituents (containing, for example, 7 – 36 carbons) can be used. Other aliphatic (including substituted aliphatic) radicals can be substituted, as is conventional. Included among these are the alkenyl and alkinyl radicals such as allyl. Fused rings (such as fused benzene or other 6-member carbocyclic rings) are preferably attached to the 4 and 5 positions; thus $R^4$ and $R^5$ together can comprise the three or four carbons or heterocyclic atoms of a fused ring. Separate aromatic rings can be substituted at the 1-, 2-, 4-, or 5- (preferably the 2-, 4-, or 5-) positions and can be monocyclic (e.g. phenyl, tolyl, xylyl, etc.) or polycyclic (preferably di- or tri-cyclic, e.g. naphthyl).

As pointed out previously, the compounds of Formula (I) are generally useful when a latent source or other controlled release of either an imidazole or sulfur dioxide is needed.

For example: alpha-cyanoacrylate monomers of the formula $CH_2 = C(CN)COOR$, wherein R can be alkyl, phenyl, alkoxy, etc., polymerize by an ionic mechanism and are sensitive to contaminants, e.g. moisture, A considerable body of patent and scientific literature is available concerning the use and storage of these monomers; see U.S. Pat. No. 2,776,232 (Shearer et al), issued Jan. 1, 1957, British Pat. No. 1,159,548 (Rice et al) published July 30, 1969, U.S. Pat. No. 3,483,870 (Coover et al), issued Dec. 16, 1969, and British Pat. No. 1,048,906 (Halpern et al), published Nov. 23, 1966. A commercially available example of a cyanoacrylate monomer is "Eastman 910", trade designation of Eastman Kodak Company. Sulfur dioxide has conventionally been used to stabilize these monomers. It has now been found that a compound of Formula (I), preferably one wherein $n = 1$, can be used as a source of constant sulfur dioxide pressure to preserve these monomers in a closed system.

The principle and practice of this invention is illustrated by the following non-limiting Examples, wherein all parts are by weight unless otherwise specified.

EXAMPLE 1

Ten grams of imidazole were placed in a 250 ml. Erlenmeyer flask and exposed to gaseous sulfur dioxide for fifteen minutes. Immediate reaction takes place as is indicated by an exotherm. A light yellow viscous liquid is obtained. An increase in weight of nine grams resulted. (This liquid will cure epoxy resins immediately and shows no latency). The viscous liquid is subsequently treated with 150 ml. $CHCl_3$ and stirred rapidly. A fine white precipitate is formed and slow evaporation of the solvent yields 18.5 gms. of product. Drying at room temperature under vacuum for three hours yields 16.5 gms. of material. (m.p. = 100° – 104°; 19.9% N; 19.8%S; [N][S] = 2.30.)

The one:one adduct of imidazole and sulfur dioxide is a latent curing agent for epoxy resins. Five parts of the adduct admixed with 95 parts of epoxy resin (Epon 828) shows no increase in viscosity over a period of months. At 100° C., this mixture has a gel time in excess of 30 minutes, whereas a similar mixture of imidazole and epoxy has a gel time of 5 minutes.

The one:one adduct shows a slow decomposition to the two:one adduct. This decomposition is shown by an almost linear decrease in sample weight over a period of about 75 hours. There was no further change in sample weight from the 80th to the 135th hour, and weightings were then discontinued.

EXAMPLE 2

Two moles (136 gm) of imidazole were placed in a three-neck flask fitted with a condenser, a gas inlet tube, and a stirrer. The imidazole was dissolved in 200 cc. of chloroform. Gaseous sulfur dioxide (one mole) was bubbled into the solution through the inlet tube as the solution was stirred. After the addition of the sulfur dioxide, stirring was continued for one hour. The solution was transferred to a Rotovapor and the solvent evaporated off at room temperature. A white solid was obtained upon removal of the solvent. (M.p. = 70° C; 21.0% N; 12.9% S; [N][S] = 3.71.) The elemental analysis indicated that the compound is $Imid_2SO_2$, where Imid = imidazole. The solid showed no weight loss over a period of months.

Five parts of the solid were added to 100 parts of "Epon" 828 (Trademark of Shell Chemical Company) resin, which is a diglycidyl ether of Bisphenol A. A portion of this mixture was immediately heated to 160° C. The sample cured to a hard resin in less than 3 minutes. The Barcol hardness of the resulting cured sample was 85. Another portion of the mixture was stored on the laboratory shelf for 3 months, during which time no change in the consistency of the resin was noted. The 3-month-old portion was warmed to 160° C., and cured at this temperature to a hard resin in less than 3 minutes. The Barcol hardness of this cured resin was 85. (A resin system is considered "cured" when it has reached the most advanced state of hardening for that system.)

EXAMPLES 3 TO 11

In Examples 3 to 7, imidazole-sulfur dioxide adducts were prepared in the same manner as Example 2 from sulfur dioxide and the following imidazoles: 1-methyl imidazole (Example 3); 2-methyl imidazole (Example 4); 1,2-dimethyl imidazole (Example 5); 2-ethyl, 4-methyl imidazole (Example 6); and benzimidazole (Example 7). Data on these compounds or adducts is set forth in Table I. The melting point of morpholine-sulfur dioxide is also given in Table I for comparison.

Examples 8 – 11 are tabulated in Table II and illustrate the use of the compounds of Examples 1, 2, 5, and 7 with a curable epoxide. The curable epoxide monomer (sometimes referred to as a "prepolymer") is "Epon" 828 (trademark of Shell Chemical Corp. for a viscous liquid diglycidyl ether of bisphenol A having an epoxide equivalent weight slightly greater than the theoretical 170 and an epoxide functionality of slightly less than 2.0). In Examples 8, 9, 10A, and 11A, 95% by weight of the liquid epoxide monomer is combined with 5% by weight of the compound of Examples 1, 2, 5, and 7, respectively; in Examples 10B and 11B 90 wt. % of the epoxide is combined with 10 wt. % of the compound of Examples 5 and 7, respectively. For comparison, data on 5 wt. % imidazole, benzimidazole, and 1,2-dimethyl imidazole are also shown in Table II; the epoxide is again " Epon" 828.

In Table II, the Barcol Hardness test is the standard 935 ASTM test. "Gel time" is a measure of the length of time a sample of resin may be maintained in a pliable form at a given temperature.

TABLE I

Adducts of Imidazoles and Sulfur Dioxide

| Ex. | Adduct | m.p. | %N (FOUND) | %S (FOUND) | [N]/[S] | %N (CALCULATED) | %S (CALCULATED) |
| --- | --- | --- | --- | --- | --- | --- | --- |
| 1. | imidazole · $SO_2$ | 100–104° | 19.9 | 19.8 | 2.30 | 21.2 | 24.2 |
| 2. | [imidazole]$_2$ · $SO_2$ | 65–70° | 21.0 | 12.9 | 3.71 | 28.0 | 16.0 |
| 3. | [1-methyl imidazole]$_2$ · $SO_2$ | 60–65° | 20.7 | 10.2 | 4.73 | 24.5 | 14.0 |
| 4. | [2-methyl imidazole]$_2$ · $SO_2$ | 60–65° | 19.3 | 12.5 | 3.51 | 24.5 | 14.0 |
| 5. | 1,2-dimethyl imidazole · $SO_2$ | 138–140° | 16.7 | 15.3 | 2.50 | 17.5 | 20.0 |
| 6. | [2-ethyl-4-methyl imidazole]$_3$ · $SO_2$ | Viscous Liquid | 14.5 | 5.6 | 5.9 | 19.7 | 11.2 |
| 7. | [benzimidazole]$_3$ · $SO_2$ | 135–140° | 18.3 | 7.5 | 5.58 | 18.7 | 10.7 |

TABLE I-continued

Adducts of Imidazoles and Sulfur Dioxide

| Ex. | Adduct | m.p. | FOUND %N | %S | [N]/[S] | CALCULATED %N | %S |
|---|---|---|---|---|---|---|---|
| 8. | 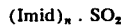 O⟨⟩N—H · $SO_2$ | 80–85° | | | | | |

*Pat. No. 2,270,490

TABLE II

| Example | Compound of | Amount (wt. %) | 100°C. | 120°C. | 140°C. | 160°C. | 180°C. | 200°C. | Barcol Hardness of Cured Product |
|---|---|---|---|---|---|---|---|---|---|
| | | | | | Examples 8–11 GEL TIME (minutes:seconds) At: | | | | |
| 8 | Example 1 | 5 | 30 min: 21 sec. | 9 min: 19 sec. | 2 min: 21 sec. | — | 1 min: 41 sec. | — | 84 |
| 9 | Example 2 | 5 | 41 min: 5 sec. | 21 min: 27 sec. | 4 min: 40 sec. | 2 min: 10 sec. | 1 min: 44 sec. | — | 84 |
| 10A | Example 5 | 5 | — | — | — | >90 min. | 93 min: 35 sec. | 85 min. | 85 |
| 10B | Example 5 | 10 | — | — | — | — | 17 min: 4 sec. | 2 min: 13 sec. | 85 |
| 11A | Example 7 | 5 | — | — | — | >90 min. | >90 min. | >90 min. | 80 |
| 11B | Example 7 | 10 | — | — | — | — | 11 min: 30 sec. | 4 min: 11 sec. | 80 |
| | imidazole | 5 | 5 min: 3 sec. | 2 min: 40 sec. | 1 min. | 24 sec. | 15 sec. | — | |
| | benzimidazole | 5 | — | — | 55 min: 18 sec. | 2 min: 40 sec. | 1 min: 11 sec. | 47 sec. | |
| | 1,2-dimethyl imidazole | 5 | — | — | 49 sec. | 41 sec. | 27 sec. | 18 sec. | |

What is claimed is:

1. A compound of the formula $(Imid)_n \cdot SO_2$ wherein
$n$ is a number from 1 to 4, and
Imid is a compound of the formula

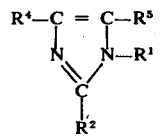

wherein $R^1$, $R^2$, $R^4$ and $R^5$ independently represent substituents selected from the group consisting of hydrogen; unsubstituted alkyl, alkenyl and alkinyl having 1 to 36 carbon atoms; phenyl; tolyl; xylyl and naphthyl, and together $R^4$ and $R^5$ can be the residue of a fused benzene ring.

2. A compound according to claim 1 wherein $R^1$, $R^2$, $R^4$ and $R^5$ independently represent substituents selected from the group consisting of unsubstituted alkyl having 1 to 36 carbon atoms and hydrogen, and together $R^4$ and $R^5$ can be the residue of a fused benzene ring.

3. A compound according to claim 1 wherein said unsubstituted alkyl substituents are lower alkyl radicals having 1 to 6 carbon atoms.

* * * * *